United States Patent [19]

Sakaguchi et al.

[11] Patent Number: 5,582,825

[45] Date of Patent: Dec. 10, 1996

[54] THERAPEUTIC MEDICINE FOR CYSTIC FIBROSIS

[75] Inventors: Kenji Sakaguchi, 11-18, Daizawa 1-chome, Setagaya-ku, Tokyo 155; Kosaku Murata; Akira Kimura, both of Kyoto; Yoshimasa Yonemoto, Tokushima; Hisako Yamaguchi, Suita; Kenichi Okayama, Toyonaka; Tetsuo Yamashita, Kagawa; Shiro Abe, Ayabe; Tomohiro Hisano, Ayabe; Minoru Nishimura, Ayabe, all of Japan

[73] Assignees: Gunze Limited, Kyoto; Otsuka Kagaku Kabushiki Kaisha, Osaka; Kenji Sakaguchi, Tokyo, all of Japan

[21] Appl. No.: 318,747

[22] PCT Filed: Feb. 24, 1993

[86] PCT No.: PCT/JP93/00227

§ 371 Date: Oct. 20, 1994

§ 102(e) Date: Oct. 20, 1994

[87] PCT Pub. No.: WO94/19006

PCT Pub. Date: Sep. 1, 1994

[51] Int. Cl.⁶ .................................................. A61K 38/45
[52] U.S. Cl. ............................................ 424/94.5; 435/193
[58] Field of Search ............................ 424/94.5; 435/193

[56] References Cited

FOREIGN PATENT DOCUMENTS

| 3-224484 | 10/1991 | Japan . |
| 4-141090 | 5/1992 | Japan . |
| WO89/01341 | 2/1989 | WIPO . |
| WO91/02796 | 3/1991 | WIPO . |

OTHER PUBLICATIONS

Brown et al., Applied and Environmental Microbiology 57(6): 1870–1872 (Jun. 1991).

Wicker-Bockelmann et al., Zbi Bakt Hyg A 266: 379–389 (1987).

Gacesa et al, Infection. Antibiot. Chemother. 42:67–71 (1989).

Hubbard et al, The New Enland Journal of Medicine, 326:812–815 (1992).

Eftekhar and Schiller, Current Microbiology, 29:37–42 (1994).

Primary Examiner—Michael G. Wityshyn
Assistant Examiner—Jean C. Witz
Attorney, Agent, or Firm—Armstrong, Westerman, Hattori, McLeland & Naughton

[57] ABSTRACT

The object of this invention is to provide a therapeutic medicine for cystic fibrosis. The therapeutic medicine for cystic fibrosis according to this invention contains an alginate lyase capable of lysing the alginate produced by strains of microorganisms of the genus Pseudomonas as the active ingredient.

10 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20
        ( B ) TYPE: amino acids
        ( D ) TOPOLOGY: linear ( i i ) MOLECULE TYPE: protein ( x i ) SEQUENCE DESCRIPTION: SEQ ID NO:1:

His Pro Phe Asp Gln Ala Val Val Lys Asp Pro Thr Ala Ser Tyr Val
1               5                   10                  15
Asp Val Lys Ala
        20

( 2 ) INFORMATION FOR SEQ ID NO:2:

( i ) SEQUENCE CHARACTERISTICS:
        ( A ) LENGTH: 20
        ( B ) TYPE: amino acids
        ( D ) TOPOLOGY: linear ( i i ) MOLECULE TYPE: protein ( x i ) SEQUENCE DESCRIPTION: SEQ ID NO:2:

His Pro Phe Asp Gln Ala Val Val Lys Asp Pro Thr Ala Ser Tyr Val
1               5                   10                  15
Asp Val Lys Ala
        20

(2) INFORMATION FOR SEQ ID NO:3:

( i ) SEQUENCE CHARACTERISTICS:
        ( A ) LENGTH: 20
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Ala Pro Ala Ala Ala His Ser Ser Ile Asp Leu Ser Lys Xaa Lys Leu
 1               5                   10                  15
Gln Ile Pro Val
         20
```

THERAPEUTIC MEDICINE FOR CYSTIC FIBROSIS

TECHNICAL FIELD

This invention relates to a therapeutic medicine for cystic fibrosis.

BACKGROUND ART

In the white population, an inherited gene-defective disease known as cystic fibrosis is encountered with a frequency of 1/1000–2000. This disease is caused by the defect of a gene coding for cystic fibrosis transmembrane conductance regulator (CFTR) protein and in the event of bacterial infection to the respiratory organ with mucoid forms of *Pseudomonas aeruginosa*,. Mucous substances collect in the lungs to cause an obstruction of airways leading to premature death. Though antibiotics and digestive enzymes are currently in use for the treatment of this disease, adequate therapeutic responses remain to be achieved as yet.

Recently (Richard C. Hubbard, et al.) have reported that symptomatic improvements in cystic fibrosis may be expected if the DNA contained in said mucus is lysed with a DNase [The New England Journal of Medicine 326, 812–815, 1992]. However, the DNase is little capable of lysing the mucus produced by bacteria of the genus Pseudomonas so that no sufficient efficacy can be expected.

Meanwhile, it is not deniable that the action of antibiotics and digestive enzymes on *Pseudomonas aeruginosa* is compromised by the alginate which these microorganisms themselves produce.

DISCLOSURE OF INVENTION

The inventors of this invention did a great deal of research to develop a therapeutically effective drug for cystic fibrosis. In the course of their exploration, the inventors discovered that the mucous substance secreted by strains of *Pseudomonas aeruginosa* isolated from the lungs of patients with cystic fibrosis contained not only DNA but also alginate in an amount several-fold as great as the amount of DNA. Inspired by the thought that should this alginate be somehow decomposed the morbidity of cystic fibrosis could be cured, the inventors did further research and have found that a certain alginate lyase is effective for the treatment of cystic fibrosis.

The object of this invention is to provide a drug suited for the therapy of cystic fibrosis.

In accordance with this invention there is provided a therapeutic medicine for cystic fibrosis which comprises an alginate lyase capable of lysing the alginate produced by microorganisms of the genus Pseudomonas as an active ingredient.

The alginate lyase that can be used as the active ingredient of the therapeutic medicine of this invention is not restricted insofar as it is able to lyse the alginate produced by microorganisms of the genus Pseudomonas. The preferred species of the-alginate lyase for the purposes of this invention include the alginate lyase having an N-terminal amino acid sequence corresponding to SEQ ID NO: 1 presented hereinafter and having the following physicochemical properties (hereinafter referred to as Al-I lyase) and the alginate lyase having an N-terminal amino acid sequence corresponding to SEQ ID NO: 2, which also appears hereinafter, and having the following physicochemical properties (hereinafter referred to as Al-III lyase), among others.

Physicochemical properties of Al-I lyase
  (1) Activity: This enzyme lyses alginate to saccharides having a non-reducing end $C_4$–$C_5$ double bond and ultimately to 4-deoxy-5-ketouronic acid.
  (2) Molecular weight: 60000
  (3) Optimal pH: 8.0
  (4) Stable pH: 6.0–8.0
  (5) Optimal temperature: 70° C.
  (6) Substrate specificity: Highly capable of lysing alginate of the bacterial origin Physicochemical properties of Al-III lyase
  (1) Activity: This enzyme lyses alginate to saccharides having a non-reducing end $C_4$–$C_5$ double bond and ultimately to 4-deoxy-5-ketouronic acid.
  (2) Molecular weight: 38000
  (3) Optimal pH: 8.0
  (4) Stable pH: 6.0–8.0
  (5) Optimal temperature: 70° C.
  (6) Substrate specificity: Very highly capable of lysing alginate of the bacterial orgin.

The above physicochemical properties are now described in detail. It should be understood that the physicochemical properties of Al-I lyase and Al-III lyase were determined using the purified enzyme samples prepared in Reference Examples 1 and 2 which are presented hereinafter.

[Alginate lyase activity]

The activity of each alginate lyase was assayed according to the principle that the saccharides having a non-reducing end $C_4$–$C_5$ double bond as produced on lysis of alginate cause a specific increase in absorbance at 235 nm.

Specifically, the enzymatic activity was determined as follows. First, 1.0 ml of a 0.2% aqueous solution of the alginate, 0.5 ml of 200 mM Tris-HCl buffer (pH 7.0) and 0.1 ml of the enzyme solution were mixed together and after the mixture was diluted with 0.4 ml of water to make 2.0 ml, the reaction was carried out at 25° C. for 5 minutes. The reaction was then stopped and the absorbance was measured at 235 nm. The enzyme activity was expressed in the activity per mg of the enzyme with the amount of enzyme increasing the absorbance at 235 nm by "1" in 1 minute being taken as unity (U).

The substrate used was the alginate harvested from a culture of the mucoid form of *Pseudomonas aeruginosa* which was isolated from the lungs of a patient with cystic fibrosis. This alginate of bacterial origin is a copolymer of o-acetylated β(1-4)-D-mannuronic acid and its C5 epimer L-glucuronic acid but unlike the seaweed type alginate derived from seaweeds such as *Eisenia bicyclis*, it has been highly acetylated.

[Molecular weight]

The molecular weight was determined by gel filtration chromatography using Sephadex G-150 (Pharmacia, Sweden). Thus, the enzyme solution was applied to a column of Sephadex G-150 equilibrated with 10 mM Tris- HCl buffer (pH 7.0) and the enzyme was eluted with the same buffer at 4° C. in 3.0 ml fractions every 4 minutes for molecular weight determination. The results are shown below in Table 1.

TABLE 1

|  | Al-I lyase | Al-III lyase |
| --- | --- | --- |
| Localization | Cytoplasm | Cytoplasm |
| Molecular weight | 60000 | 38000 |
| Subunit | 1 | 1 |

[Effects of pH and temperature]

The data are presented below in Table 2.

TABLE 2

|  | Al-I lyase | Al-III lyase |
|---|---|---|
| Optimal pH | 8.0 (Tris-HCl) | Same as left |
| Stable pH | 6.0–8.0 | Same as left |
| Optimal temperature pH 7) | 70° C. (Tris-HCl, | Same as left |
| Stable temperature pH 7) | ≦40° C. (Tris-HCl, | Same as left |

[Amino acid analysis]

The N-terminal amino acid sequence of each enzyme was determined using a protein sequencer (tradename: Biosystem 477A, Applied Biosystems, USA) linked to an amino acid derivative analyzer (tradename: Biosystem 120A PTH analyzer, Applied Biosystems, USA). The N-terminal amino acid sequences are shown below.

The N-terminal amino acid sequence of Al-I lyase:
His-Pro-Phe-Asp-Gln-Ala-Val-Val-Lys-Asp-Pro-Thr-Ala-Ser-Tyr-Val-Asp-Val-Lys-Ala- (Seq. ID NO: 1)

The N-terminal amino acid sequence of Al-III lyase:
His-Pro-Phe-Asp-Gln-Ala-Val-Val-Lys-Asp-Pro-Thr-Ala-Ser-Tyr-Val-Asp-Val-Lys-Ala- (Seq. ID NO: 2)

[Substrate specificity]

Al-I lyase: Highly capable of lysing alginate of the bacterial origin

Al-III lyase: Very highly capable of lysing alginate of the bacterial origin

[Effect of chemicals]

The data are presented below in Table 3.

TABLE 3

|  | Al-I lyase | Al-III lyase |
|---|---|---|
| HgCl$_2$ (1.0 mM) | + | + |
| CuCl$_2$ (5.0 mM) | + | + |
| FeCl$_2$ (5.0 mM) | + | + |
| Glutathione (10 mM) | − | − |
| Dithiothreitol (10 mM) | − | − |
| Ethylenediamine tetraacetate (10 mM) | − | − |

+ inhibited,
− not inhibited

The Al-I lyase and Al-III lyase for use in this invention can be produced by cultivating *Flavobacterium* sp. OTC-6, as isolated from soil, in an alginate-containing medium.

*Flavobacterium* sp. OTC-6 is a novel microorganism never described in the literature before and has been deposited on Feb. 15, 1993 with the National Institute for Bioscience and Human Technology at 1-3, Higashi 1 chome, Tsukuba-shi, Ibaraki-ken 305 JAPAN, under the accession number of FERM BP-4189.

The bacteriological characteristics of this organism are shown below.

(a) Morphology:

(1) Cell shape and size: rods (0.3–0.6)×(1.0–1.2) μm (2) Motility: nonmotile (3) Flagellation: non-flagellated (4) Sporogenesis: non-sporulating (5) Gram's stain: negative (b) Cultural characteristics:

(1) Broth agar plate culture:
After 24 hours of incubation at 30° C., round colonies 1–2 mm in diameter are formed. The colonies are solid and white.

(2) Standard agar plate culture:
After 24 hours of incubation at 30° C., round colonies 1–2 mm in diameter are formed. The colonies are solid and light yellow.

(3) Litmuth milk culture:
Incubation at 30° C. does not cause coagulation. The color is blue-purple and unchanged.

(c) Physiological characteristics (1) Catalase: positive (2) Oxidase: positive (3) Urease: negative (4) Phosphatase: negative (5) OF test: negative (6) VP test: negative (7) Indole production: negative (8) Hydrogen sulfide production: negative (9) Production of acid from sugars:
Positive: glucose
Negative: arabinose, cellobiose, lactole, mannitol, raffinose, sucrose, xylose, glycerole, fructose, maltose, rhamnose

(10) Hydrolysis of starch: negative

(11) Hydrolysis of gelatin: negative

(12) Hydrolysis of esculin: negative

(13) Reduction of nitrate: positive

(14) pH for growth: 5.0–8.5

(15) Optimal temperature for growth: 28°–34° C.

(16) NaCl concentration for growth: 0–1%

(d) GC content of DNA: 63%

Cultivation of *Flavobacterium* sp. OTC-6 can be carried out in the same manner as the culture of ordinary bacteria and is preferably performed in a liquid medium under aeration and agitation. Furthermore, in order to cause this organism to produce the object enzyme, it is generally preferable to carry out a mass culture of the order of ten and odd to several hundred liters or even more.

The culture medium is preferably added alginate as a component. The amount of alginate is not particularly restricted but, generally speaking, is preferably about 0.1–2 weight % based on the total amount of the medium. Furthermore, the culture medium for use in this invention may contain, in addition to alginate, those sources of carbon and nitrogen and inorganic salts which are generally used in the cultivation of bacteria. Among said sources of carbon is glucose. Organic nitrogenous substances such as peptone, meat extract, corn steep liquor, yeast extract, etc. and inorganic nitrogen compounds such as ammonium sulfate, ammonium chloride, etc. can be used as said sources of nitrogen. The inorganic salts may for example be potassium dihydrogen phosphate, dipotassium hydrogen phosphate, magnesium sulfate and sodium chloride.

Cultivation is carried out at a temperature of about 25°–40° C. under the pH conditions of about 5.5–8.0 and is generally completed in about 24–48 hours. As the resulting culture broth is purified by the per se known means, there is obtained the object alginate lyase. For example, a cell extract separated from the broth is purified by column chromatography using DEAE-cellulose, Sephadex G-150, or hydroxylapatite, for instance.

In using said alginate lyase as a therapeutic medicine for cystic fibrosis, it can be formulated into various pharmaceutical compositions using special care not to cause inactivation of the enzyme. It is essential to avoid applying excessive heat or using a carrier tending to deactivate the enzyme.

Thus, it is recommendable to use such additives as polyethylene glycol, physiological saline, phosphate buffer, etc. in the manufacture of a spray or solution, such additives as starch, lactose, etc. in the manufacture of tablets or powders, such additives as olive oil, polyethylene glycol, etc. in the manufacture of an emulsion, or such additives as hard gelation etc. in the manufacture of capsules.

It is also within the scope of this invention to incorporate a bronchodilator such as aminophylline, an antibiotic drug such as a penicillin, cephem or new quinolone, a DNase, a protease inhibitor and/or an amiloride in suitable amounts for enhanced therapeutic efficacy.

The unit dosage form of such a pharmaceutical composition of this invention can be chosen according to the therapeutic objective, and includes a spray, infusion, tablet, solution, emulsion, powder, capsule, injection and so on.

There is no particular limitation on the modality of treatment with the pharmaceutical composition of this invention and the composition can be administered according to a treatment protocol which depends on the patient's age, sex and other factors, the severity of disease and so on. By way of illustration, a spray or an infusion is directly applied to the affected site by spraying or infusion. The tablet, solution, emulsion, powder and capsule are administered orally. The injection is administered intravenously, either as it is or in admixture with an ordinary infusion fluid such as glucose solution, amino acid infusion and so on.

The dosage of the pharmaceutical composition of this invention can be judiciously selected according to the method of administration, sex and other patient factors, the severity of disease, etc. but in terms of the active ingredient alginate lyase, the daily dose per kg body weight is generally 0.1–100 mg and preferably 1–10 mg.

BEST MODE FOR CARRYING OUT THE INVENTION

The following reference examples, pharmacological test examples and formulation example are intended to describe the invention in further detail.

Reference Example 1 (Preparation of Al-I lyase)

*Flavobacterium* sp. OTC-6 was inoculated into 10 l of an autoclaved liquid medium (containing 1.50% of sodium alginate, 0.10% of ammonium sulfate, 0.05% of magnesium sulfate septahydrate, 0.10% of potassium dihydrogen phosphate, 0.40% of disodium hydrogen phosphate 12 hydrate, and 0.05% of yeast extract; pH 7.2) and cultivated under shaking at 30° C. for 24 hours. The resulting broth was centrifuged to harvest 73 g of cells. The cells were suspended in 60 ml of 10 mM Tris-HCl buffer (pH 7.0), sonicated (9 KHz, 170 W, 10 min.) and centrifuged (25000 G, 30 min.) to separate a supernatant (cell extract).

This cell extract (120 ml, protein 6.68 g) was purified using a column of DEAE-cellulose (Wako Pure Chemical) equilibrated with 10 mM Tris-HCl buffer (pH 7.0) (4 cm×25 cm, 0–0.5M NaCl linear gradient elution).

The resulting active fraction (250 ml, protein 1.78 g) was further purified using a column of hydroxylapatite (Tosoh) equilibrated with 5.0 mM potassium phosphate buffer (hereinafter referred to as KPB) (pH 7.0) (4 cm×25 cm, 5–500 mM KPB linear gradient elution, pH 7.0) and the eluate was concentrated (20 ml, protein 208 mg) using a ultrafilter membrane (Amicon PM10, Grace Japan).

The concentrate was passed through a column (2.5 cm×60 cm) of Sephadex G-150 (Pharmacia, Sweden) equilibrated with 10 mM Tris-HCl buffer (pH 7.0) and the active fraction (75 ml, protein 191 mg) was further purified on a column of QAE-Sephadex A-25 (Pharmacia) equilibrated with 10 mM Tris-HCl buffer (pH 7.0) (2.5 cm×30 cm, 0–0.5M NaCl linear gradient elution). This product was designated as Al-I lyase.

Reference Example 2 (Preparation of Al-III lyase)

Using a two-ton fermentation tank, 1400 l of an autoclaved liquid medium (containing 1.00% of sodium alginate, 0.01% of ammonium sulfate, 0.05% of magnesium sulfate septahydrate, 0.10% of potassium dihydrogen phosphate, 0.40% of disodium hydrogen phosphate 12-hydrate and 0.05% of yeast extract; pH 7.2) was inoculated with *Flavobacterium* sp. OTC-6 at 1.2% inoculation level and the inoculated medium was incubated at 30° C. for 17 hours. This cultural procedure was carried out under agitation (170 rpm) and air sparging at a flow rate of 200 l/min. The cells (350 g) harvested from the culture broth amounting to 100 l were suspended in 5 l of 5.0 mM KPB (pH 7.0) and the suspension was passed through a cell disintegrator (Dyno-Mill-KDL, Shinmaru Enterprises Corporation) and centrifuged (25000 G, 30 min.) to separate a supernatant (cell extract).

This cell extract (5.54 l, protein 51.2 g) was passed through a column (4.6 cm×18 cm) of DEAE-Cellulofine (Seikagaku Kogyo) equilibrated with 5.0 mM KPB (pH 7.0) and an active fraction was obtained as the effluent (6.05 l, protein 18.9 g).

This fraction was purified by column chromatography using a column (12 cm×18 cm) of hydroxylapatite (Nacalai Tesque) equilibrated with 5.0 mM KPB (pH 7.0) by the stepwise elution method (20 mM, 40 mM and 100 mM KPB, pH 7.0).

The Al-III-containing fraction (2.64 l, protein 984 mg) eluted with 40 mM KPB (pH 7.0) was saturated 40% with ammonium sulfate and purified using a column of Butyl-Sepharose F.F. (Pharmacia) equilibrated with 5.0 mM KPB (pH 7.0) similarly saturated 40% with ammonium sulfate (4.6 cm×10 cm, 40–0% ammonium sulfate-saturated 5.0 mM KPB linear gradient elution, pH 7.0).

The resulting active fraction was concentrated (66 ml, protein 218 mg) using a ultrafilter membrane (Amicon PM10, Grace Japan) and passed through a column (5.0 cm×60 cm) of Sephacryl S-200 HR (Pharmacia) equilibrated with 5.0 mM KPB (pH 7.0). The resulting active fraction (176 ml, protein 153 mg) was passed through a column (4.6 cm×6.0 cm) of S-Sepharose F. F. (Pharmacia) equilibrated with 5.0 mM KPB (pH 7.0) and linear pH gradient elution [5.0 mM KPB (pH 7.0)-5.0 mM dipotassium hydrogen phosphate (pH 8.6)] was carried out. The active fraction thus obtained was designated as Al-III lyase.

Reference Example 3 (Preparation of Al-II lyase)

*Flavobacterium* sp. OTC-6 was inoculated into 12 l of an autoclaved liquid medium (containing 0.20% of sodium alginate, 0.10% of ammonium sulfate, 0.05% of magnesium sulfate septahydrate, 0.10% of potassium dihydrogen phosphate, 0.40% of disodium hydrogen phosphate 12-hydrate and 0.05% of yeast extract; pH 7.2) and cultivated aerobically at 30° C. for 24 hours. The resulting broth was centrifuged to harvest 60 g of cells.

The cells were suspended in 100 ml of 5 mM Tris-HCl buffer (pH 7.0), sonicated (9 KHz, 10 min., 0° C.) and centrifuged (25000 G, 30 min.) to separate a supernatant (cell extract). This cell extract (160 ml, protein 4.97 g) was purified using a column of CM-cellulose equilibrated with 10 mM Tris-HCl buffer (pH 7.0) (4.6 cm×46 cm; 0–0.6M NaCl linear gradient elution). The resulting active fraction (1235 ml, protein 608 mg) was further purified with a column of hydroxylapatite (Nacalai Tesque) equilibrated with 5.0 mM KPB (pH 7.0) (4.6 cm×26 cm; 5–500 mM KPB linear gradient elution; pH 7.0).

The resulting active fraction (284 ml, protein 34.8 mg) was saturated 30% with ammonium sulfate and purified using a column of Butyl-Toyopearl 650M (Tosoh) equilibrated with 5.0 mM KPB (pH 7.0) similarly saturated 30% with ammonium sulfate (1.5 cm×15 cm, 30–0% ammonium sulfate-saturated 5.0 mM KPB linear gradient elution; pH 7.0).

*Eisenia bicyclis* as manufactured by Sigma Chemical, USA as the standard. The DNA was assayed by the diphenylamine method using salmon testicular DNA (Sigma Chemical) as the standard. As the alginate lyase, the Al-I lyase, Al-II lyase and Al-III lyase prepared in the above Reference Examples were respectively used.

The activities of these enzymes were respectively assayed by the alginate lyase assay method described hereinbefore.

The results are presented in Table 4.

TABLE 4

| Strain | Cell weight *1) (g) | DNA *2) (mg) | Alginate *3) (mg) | Specific activity (U/mg) *4) | | |
|---|---|---|---|---|---|---|
| | | | | Al-I lyase | Al-III lyase | Al-II lyase |
| 1 | 1.22 | 22.3 | 234 | 68.3 | 125 | 0 |
| 2 | 1.29 | 30.1 | 228 | 62.1 | 132 | 0 |
| 3 | 0.83 | 58.4 | 195 | 59.8 | 109 | 0 |
| 4 | 1.62 | 32.3 | 50.3 | 62.5 | 128 | 0 |
| 5 | 1.43 | 80.1 | 155 | 64.3 | 113 | 0 |
| 6 | 1.21 | 7.8 | 60.1 | 59.8 | 133 | 0 |
| 7 | 1.32 | 8.3 | 49.2 | 52.5 | 127 | 0 |
| A | — | — | — | 63.3 | 132 | 0 |
| Sodium alginate | | | | 134 | 30 | 146 |

The active fraction thus obtained was concentrated (5 ml, protein 10 mg) using a ultrafilter membrane (Amicon PM10, Grace Japan), passed through a column (2.6 cm×74 cm) of Toyopearl HW-55 (Tosoh) equilibrated with 5.0 mM KPB (pH 7.0), and concentrated again with a ultrafilter membrane. The product was designated as Al-II lyase.

The Al-II lyase prepared as above has an N-terminal amine acid sequence corresponding to SEQ ID NO: 3, which appears hereinafter, and has the following physicochemical properties. These physicochemical properties were determined by the methods already described for the alginate lyases Al-I and Al-III.

(1) Activity: This enzyme lyses alginate to saccharides having a non-reducing end $C_4$–$C_5$ double bond and ultimately to 4-deoxy-5-ketouronic-acid.

(2) Molecular weight: 25000

(3) Optimal pH: 8.0

(4) Stable pH: 6.0–8.0

(5) Optimal temperature: 70° C.

(6) Substrate specificity: The enzyme acts on alginate, showing a particularly high lytic action on the alginate derived from *Eisenia bicyclis*.

Pharmacological Test Example 1

The mucoid form of *Pseudomonas aeruginosa* was isolated from cystic fibrosis patients by Dr. A. Prince at Colombia University. All the species (7 species) of this mucoid form of *Ps. aeruginosa* were aerobically cultivated in 100 ml of TSB (Tryptic Soy Broth, Difco Laboratories, USA) at 30° C. for 20 hours. The cells were removed by centrifugation and 4 volumes of 95% ethanol was added to the supernatant. The mixture was allowed to stand at 4° C. for 3 hours and the sediment was centrifugally collected and washed with 95% ethanol twice and, then, with 100% ethanol. The sediment was dried in vacuo at room temperature to provide a bacterial alginate. This alginate was dissolved in water and used as the substrate for the assay of alginate lyase activity.

The alginate was quantitated by the carbazole method using the sodium alginate (molecular weight 25700) from In Table 4 above, *1) denotes the weight of the moist cells harvested from 100 ml of the broth, *2) denotes the amount of DNA accumulated in 100 ml of the broth, *3) denotes the amount of alginate accumulated in 100 ml of the broth, and *4) denotes the activity per mg of the enzyme as calculated with the amount of enzyme increasing the absorbance at 235 nm by "1" in 1 minute being taken as unity (U). The symbol A in the Strain column represents the alginate harvested from a culture of the mucoid form of *Pseudomonas aeruginosa* isolated by Dr. A. M. Chakrabarty, and sodium alginate represents the sodium salt of alginate derived from *Eisenia bicyclis* as manufactured by Sigma Chemical.

The following can be seen from Table 4. Thus, whereas Al-II lyase shows no activity against any of the alginates produced by said 7 species of the mucoid form of *Ps. aerugionosa*, Al-I lyase and Al-III lyase show activity on all of these alginates and Al-III lyase, in particular, is remarkably active on the alginates. Since Al-I lyase and Al-III lyase show high substrate specificity for the alginates responsible for the mucus in patients with cystic fibrosis as demonstrated above, they are suggested to be effective in the treatment of cystic fibrosis.

Pharmacological Test Example 2

To the mucous substance produced by the mucoid form of *Pseudomonas aeruginosa* isolated from a cystic fibrosis patient was added the Al-I lyase prepared in Reference Example 1 above and the change in viscosity of the mucus was investigated. Thus, 20 μg of Al-I lyase was added to 20 ml of the mucous substance produced by Strain 1 mentioned in Table 4 above (containing 46.8 mg of alginate and 4.46 mg of DNA) and the viscosity of the mucus was serially measured with a viscosimeter at 25° C. FIG. 1 diagrammatically shows the time course of viscosity of the mucous substance after addition of Al-I lyase.

For comparison's sake, 20 μg each of DNase I and DNase II (Sigma Chemical) were added to 20 ml of the above mucus, 20 μg of the Al-II lyase prepared in Reference Example 3 above was added to 20 ml of the same mucus as above and the change in viscosity of the mucous substance in each case was investigated. FIG. 2 diagrammatically shows the time course of viscosity of the mucous substance after addition of DNase I and DNase II. FIG. 3 diagrammatically shows the time course of viscosity of the mucous substance when Al-II lyase was added. FIG. 4 diagrammatically shows the time courses of viscosity of the mucous substance over a period of 60 minutes following addition of each enzyme.

It is clear from FIGS. 1 and 4 that addition of Al-I lyase causes a rapid decrease in viscosity of the mucous substance. It was also confirmed that by 1 hour following addition of Al-I lyase, the viscosity of the mucous substance had dropped to a level comparable to the viscosity of water. However, when any of DNase I, DNase II and Al-II lyase was added, the viscosity of the mucus was not decreased at all.

Formulation Example

In a 150 mM sodium chloride-1 mM calcium chloride solution was dissolved 4 mg/ml of the Al-III lyase prepared in Reference Example 2 above to provide a spray preparation.
Sequence Table
Sequence Number: 1
Sequence length: 20
Sequence type: amino acids
Topology: linear
Molecule type: protein
Sequence:
His Pro Phe Asp Gln Ala Val Val Lys Asp Pro Thr Ala Ser Tyr Val Asp Val Lys Ala
Sequence Number: 2
Sequence length: 20
Sequence type: amino acids
Topology: linear
Molecule type: protein
Sequence:
His Pro Phe Asp Gln Ala Val Val Lys Asp Pro Thr Ala Ser Tyr Val Asp Val Lys Ala
Sequence Number: 3
Sequence length: 20
Sequence type: amino acids
Topology: linear
Molecule type: protein
Sequence:
Ala Pro Ala Ala Ala His Ser Ser Ile Asp Leu Ser Lys Xaa Lys Leu Gln Ile Pro Val

---

Figure 1:
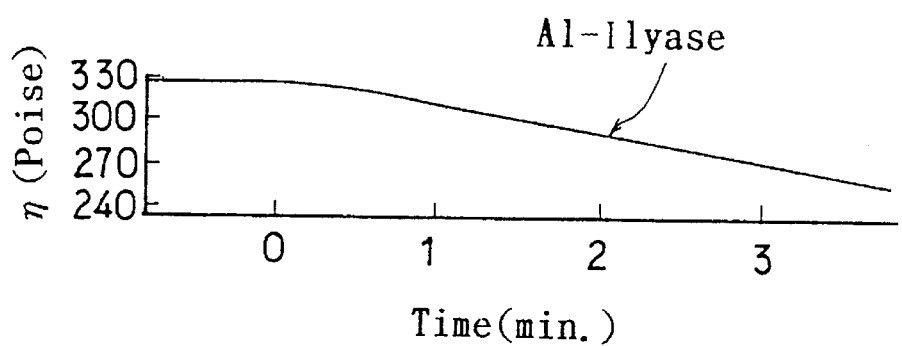
FIG. 1 is a graph showing the time course of viscosity of the mucous substance after addition of Al-I lyase.
Figure 2:
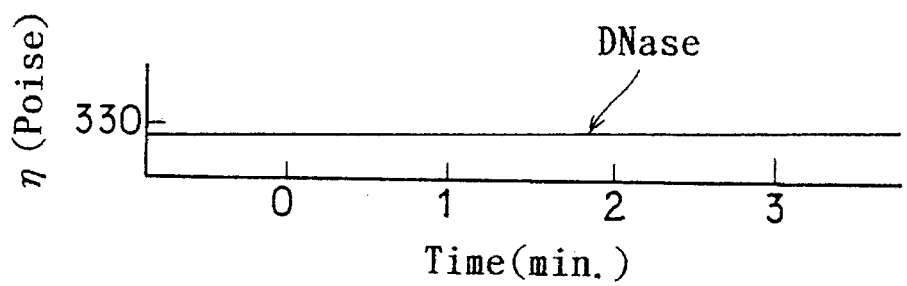
FIG. 2 is a graph showing the time course of viscosity of the mucous substance after addition of DNase I and DNase II.
Figure 3:
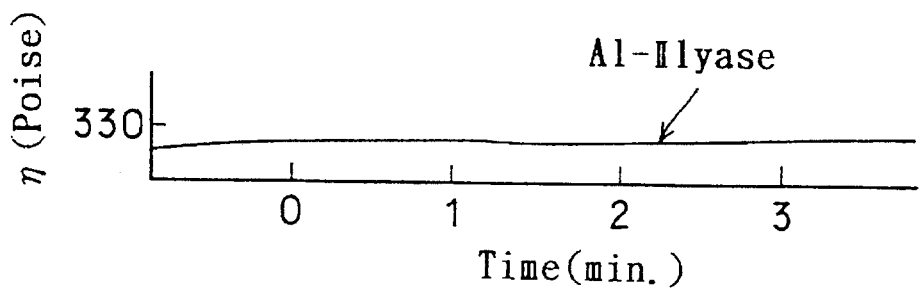
FIG. 3 is a graph showing the time course of viscosity of the mucous substance after addition of Al-II lyase.
Figure 4:
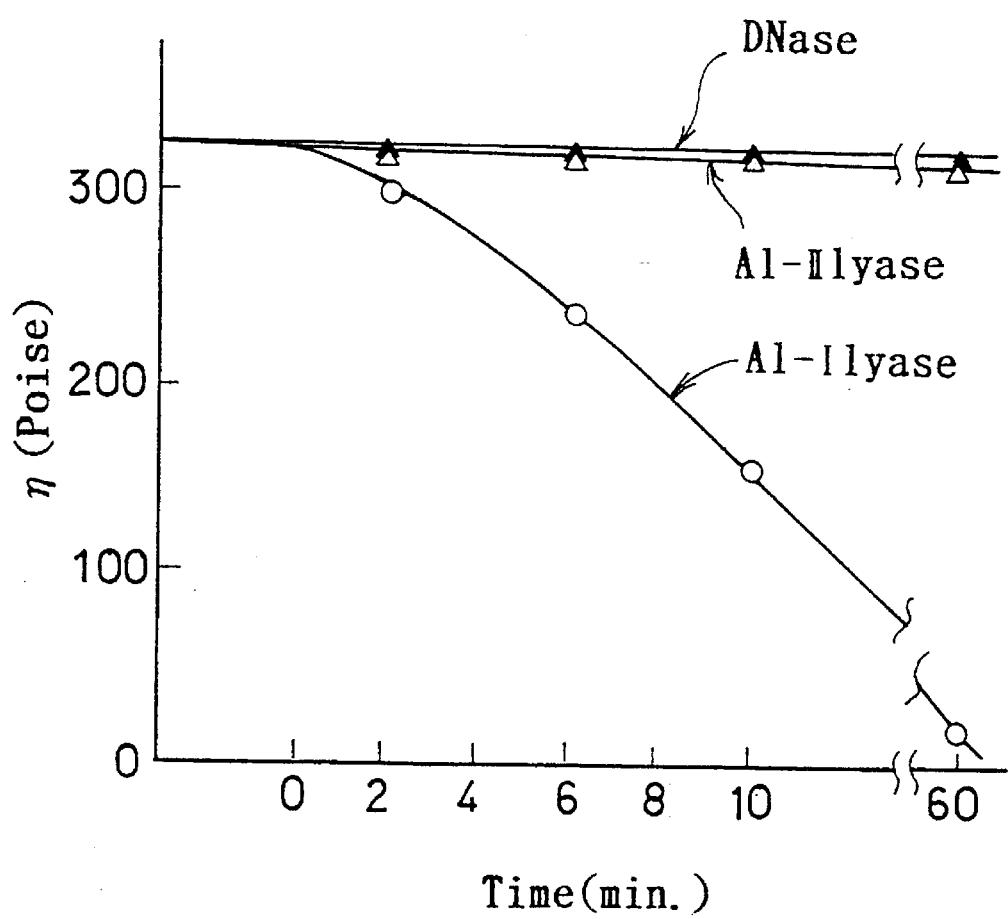
FIG. 4 is a graph showing the changes in viscosity of the mucous substance over a period of 60 minutes following addition of Al-I lyase, DNase (DNase I and DNase II) and Al-II lyase, respectively.

We claim:

1. An isolated alginate lyase enzyme wherein said enzyme is capable of lysing alginate in the mucous substance produced in a patient with cystic fibrosis and wherein said enzyme has an N-terminal amino acid sequence corresponding to SEQ ID No.: 1, may be obtainable from *Flavobacterium* OTC-6 and has the following physicochemical properties:

(1) Activity: lyses alginate to saccharides having a non-reducing end $C_4$–$C_5$ double bond and ultimately to 4-deoxy-5-ketouronic acid;

(2) Molecular weight: 60,000;

(3) Optimal pH: 80;

(4) Stable pH: 6.0–8.0;

(5) Optimal temperature: 70° C.;

(6) Substrate Specificity: alginate.

2. An isolated alginate lyase enzyme wherein said enzyme is capable of lysing alginate in the mucous substance produced in a patient with cystic fibrosis and wherein said enzyme has an N-terminal amino acid sequence corresponding to SEQ ID No.: 2, may be obtainable from *Flavobacterium* OTC-6 and has the following physicochemical properties:

(1) Activity: lyses alginate to saccharides having a non-reducing end $C_4$–$C_5$ double bond and ultimately to 4-deoxy-5-ketouronic acid;

(2) Molecular weight: 38,000;

(3) Optimal pH: 8.0;

(4) Stable pH: 6.0–8.0;

(5) Optimal temperature: 70° C.;

(6) Substrate Specificity: alginate with a particularly high lytic activity on alginate of the bacterial origin.

3. A pharmaceutical composition for the treatment of cystic fibrosis comprising an effective amount of the enzyme of claim 1 and a pharmaceutically acceptable carrier or diluent.

4. A pharmaceutical composition for the treatment of cystic fibrosis comprising an effective amount of the enzyme of claim 2 and a pharmaceutically acceptable carrier or diluent.

5. The pharmaceutical composition of claim 3 further comprising a DNase or an antibiotic.

6. The pharmaceutical composition of claim 4 further comprising a DNase or an antibiotic.

7. The pharmaceutical composition as claimed in any one of claims 3, 4, 5 or 6 which is provided in a unit dosage form of spray, solution or emulsion.

8. A method of treating cystic fibrosis comprising administering an effective amount of the pharmaceutical composition of claim 7 by spraying or coating to the affected site.

9. The pharmaceutical composition of any one of claims 3, 4, 5 or 6, wherein the enzyme is capable of lysing a highly acetylated alginate compared with an alginate derived from seaweeds, the acetylated alginate being one produced by the microorganisms of the genus Pseudomonas, the alginate lyase being present in an effective amount capable of lysing the alginate in mucous substance produced in a patient with cystic fibrosis.

10. A method of treating cystic fibrosis comprising administering an effective amount of the enzyme of claim 1 or claim 2 by spraying or coating to the affected site.

\* \* \* \* \*